United States Patent
Korporaal

(10) Patent No.: US 9,271,656 B2
(45) Date of Patent: Mar. 1, 2016

(54) PREDICTION OF A LIKELY CONTRAST MEDIUM BEHAVIOR

(71) Applicant: SIEMENS AKTIENGESELLSCHAFT, Munich (DE)

(72) Inventor: Johannes Georg Korporaal, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 100 days.

(21) Appl. No.: 14/149,919

(22) Filed: Jan. 8, 2014

(65) Prior Publication Data

US 2014/0206991 A1  Jul. 24, 2014

(30) Foreign Application Priority Data

Jan. 24, 2013  (DE) .................. 10 2013 201 136

(51) Int. Cl.
*A61B 5/026* (2006.01)
*A61B 5/0245* (2006.01)
(Continued)

(52) U.S. Cl.
CPC ............... *A61B 5/026* (2013.01); *A61B 5/0275* (2013.01); *A61B 5/7275* (2013.01); *A61B 6/481* (2013.01);
(Continued)

(58) Field of Classification Search
CPC .... A61B 5/0245; A61B 5/026; A61B 5/0275; A61B 5/7275; A61B 6/032; A61B 6/481; A61B 6/488; A61B 6/503; A61B 6/504; A61B 6/507; A61B 6/5217
See application file for complete search history.

(56) References Cited

U.S. PATENT DOCUMENTS 7,477,929 B2  1/2009  Klotz et al.
8,280,492 B2  10/2012  Niethammer
(Continued)

FOREIGN PATENT DOCUMENTS

CN         1820710 A      8/2006
DE    102005006657 A1     8/2006
(Continued)

OTHER PUBLICATIONS

Fleischmann Dominik et al.: "Mathematical Analysis of Arterial Enhancement and Optimization of Bolus Geometry for CT Angiography Using the Discrete Fourier Transform"; in: Journal of Computer Assisted Tomography, Lippincott Williams & Wilkins; 1999, vol. 23, No. 3. pp. 474-484; 1999.

Kligfield Paul et al.: "Recommendations for the Standardization and Interpretation of the Electrocardiogram"; Part I: The Electrocardiogram and Its Technology; in: J. Am. Coll. Cardiol. (JACC); vol. 49; No. 10; pp. 1109-1127; DOI:10.1016/j.jacc.2007.01.024; 2007; Mar. 13, 2007.

(Continued)

*Primary Examiner* — Michael Rozanski
(74) *Attorney, Agent, or Firm* — Harness, Dickey & Pierce, P.L.C.

(57) ABSTRACT

A method is disclosed for the prediction of a likely contrast medium behavior for a contrast medium-assisted examination of an object under investigation. In an embodiment, the method includes detecting patient-specific blood flow behavior data in a pre-measurement making use of a defined examination protocol and determining an individual impulse response function from the blood flow behavior data; detecting a pre-measured heart rate signal associated with the pre-measurement; and predicting the likely contrast medium behavior based on the individual impulse response function, the pre-measured heart rate signal and a current examination protocol, and a currently detected heart rate signal. A method for activation of a medical imaging system is also disclosed. Also disclosed are a device for predicting a likely contrast medium behavior, a control device with a device of this type for an imaging system, and an imaging system with a control device.

15 Claims, 9 Drawing Sheets

(51) Int. Cl.
*A61B 6/00* (2006.01)
*A61B 5/0275* (2006.01)
*A61B 5/00* (2006.01)
*A61B 6/03* (2006.01)

(52) U.S. Cl.
CPC .............. *A61B 6/488* (2013.01); *A61B 6/507* (2013.01); *A61B 5/0245* (2013.01); *A61B 6/032* (2013.01); *A61B 6/503* (2013.01); *A61B 6/504* (2013.01); *A61B 6/5217* (2013.01)

(56) References Cited

U.S. PATENT DOCUMENTS

| | | |
|---|---|---|
| 9,050,055 B2 * | 6/2015 | Korporaal |
| 2006/0178836 A1 | 8/2006 | Bai et al. |
| 2006/0239917 A1 | 10/2006 | Klotz et al. |
| 2007/0167750 A1 | 7/2007 | Niethammer |
| 2008/0097197 A1 | 4/2008 | Kalafut et al. |
| 2010/0030073 A1 | 2/2010 | Kalafut |
| 2010/0204572 A1 | 8/2010 | Kalafut et al. |
| 2013/0324845 A1 | 12/2013 | Korporaal |

FOREIGN PATENT DOCUMENTS

| | | |
|---|---|---|
| DE | 102006055167 A1 | 7/2007 |
| DE | 102012209410 A1 | 12/2013 |

OTHER PUBLICATIONS

The CSE Working Party; "Recommendations for measurement standards in quantitative electrocardiography", in: European Heart Journal (1985); No. 6, pp. 815-825; 1985.

Willems J. L. et al: Common Standards for Quantitative Electrocardiography: Goals and Main Results; in: Methods of Information in Medicine; vol. 29; pp. 263-271; 1990.

Mahnken Andreas H.: "Quantitative prediction of contrast enhancement from test bolus data in cardiac MSCT", in: Eur. Radiol. 2007, vol. 17, pp. 1310-1319; 2007.

Kim S. M. et al: "Interindividual variablility of arterial impulse response to intravenous injection of nonionic contrast agent (Iohexol) in DCE-CT study", in: Medical Physics 2009; vol. 36; No. 10; pp. 4791-480; DOI:10.1118/1.3224495.

Eisa Fabian et al.: "Optical tracking of contrast medium bolus to optimize bolus shape and timing in dynamic computed tomography"; in:Physics in Medicine and Biology; vol. 57; pp. N173 bis N182; doi:10.1088/0031-9155/57/10/N173; 2012.

German Priority Document for German Application 10 2013201136.9.

First Office Action issued by the Chinese Patent Office dated Sep. 2, 2015 for CN Patent Application No. 2014100224869.

* cited by examiner

PREDICTION OF A LIKELY CONTRAST MEDIUM BEHAVIOR

PRIORITY STATEMENT

The present application hereby claims priority under 35 U.S.C. §119 to German patent application number DE 102013201136.9 filed Jan. 24, 2013, the entire contents of which are hereby incorporated herein by reference.

FIELD

At least one embodiment of the invention generally relates to a method and/or a device for the prediction of a likely contrast medium behavior for a contrast medium-assisted examination of an object under investigation, in particular an embodiment relates to a contrast medium-assisted imaging method, preferably in the context of an angiographic examination procedure on a patient. At least one embodiment of the invention also generally relates to a method for activation of a medical imaging system, a control device for an imaging system and/or an imaging system with a control device of this type.

BACKGROUND

The older patent application DE 10 2012 209 410.5 discloses a method for determining an individual patient-specific contrast medium impulse response function (known hereinafter, for short, as "impulse response function" or "patient function") based on test bolus data, with which a prediction of the contrast medium behavior can later be created in the context of a contrast medium-assisted imaging measurement.
This patient function describes the cardiovascular properties of the patient at the time point when the test bolus was measured. In principle, the contrast medium behavior could be predicted for any desired injection protocol under the assumption that the individual patient function is still valid at the later time point. An injection protocol is a precise time-related stipulation according to which the quantity of contrast medium is administered to the patient and includes, for example, the starting time point, the flow rate and the end time point of the contrast medium administration.

Algorithms for this purpose, referred to as contrast enhancement prediction (CEP) algorithms, are generally known from a variety of publications such as, for example:

Dominik Fleischmann et al., "Mathematical Analysis of Arterial Enhancement and Optimization of Bolus Geometry for CT Angiography Using the Discrete Fourier Transform", Journal of Computer Assisted Tomography, 1999, vol. 23, No. 3, pages 474 to 484, and Andreas H. Mahnken et al., "Quantitative prediction of contrast enhancement from test bolus data in cardiac MSCT", Eur. Radiol. 2007, 17, pages 1310 to 1319.

These CEP algorithms calculate the likely behavior of the contrast medium in the patient and are usually constructed from two sub-algorithms. A first sub-algorithm determines a patient-specific contrast medium impulse response function (or arterial impulse response, AIR) and is known as the "AIR algorithm". The second sub-algorithm calculates a prediction of the likely contrast medium behavior in the patient and is known as the "PRED algorithm". A CEP algorithm therefore usually includes a combination of an AIR algorithm and a PRED algorithm.

In all these known methods, the patient being examined is regarded as being a linear time-invariant (LTI) system. This means, in general, that the contrast medium accumulation in the patient C(t) can be expressed mathematically as a convolution of the injection protocol IF(t) with the impulse response function or patient function AIR(t):

$$C(t)=IF(t) \otimes \mathrm{AIR}(t) \qquad [1]$$

As a consequence, the CEP algorithms carry out all the calculations in the time domain and/or the Fourier domain which is derived from the time domain.

However, this is based on the assumption that the driving force for the contrast medium, the blood circulation, is invariable and stable over time. However, this is often not the case.

A typical area of application for contrast medium-assisted imaging methods is, for example, CT angiography (CTA), that is, the imaging of the vessels by way of computed tomography. A CTA scan is an operation of a computed tomography scanner to image the vessels, and a heart CTA or heart scan is the imaging of the heart and representation of the heart vessels.

It can occur, in heart scans during CT angiography (CTA), in particular, that the heart rate (number of heartbeats per time interval) is lastingly raised or lowered following the test bolus, for example, under the influence of beta blockers (e.g. metoprolol), which are typically administered shortly before the scan to patients with a raised heart rate. Since the recirculation time of the blood changes at a different heart frequency, the patient function also changes in this case. This would lead to an imprecise prediction of the contrast medium behavior.

SUMMARY

At least one embodiment of the invention is directed to a method and/or a device for the prediction of a likely contrast medium behavior in a contrast medium-assisted examination, in particular a contrast medium-assisted imaging method, preferably in the context of an angiographic examination method of the aforementioned type such that particularly in the case of irregular heart rates, better prediction of the contrast medium behavior at a later time point is enabled, particularly if the heart rate has changed between the delivery of the test bolus and the actual later examination.

A method is disclosed and a device is disclosed.

In the method according to at least one embodiment of the invention, in order to predict a likely contrast medium behavior for a contrast medium-assisted examination of an object under investigation (hereinafter known, without restricting the generality thereof, as the "patient", for which reason the expression "patient-specific" is also used instead of the expression "investigation object-specific"), at least the following is carried out:

firstly, in a pre-measurement, patient-specific blood flow behavior data are determined using a defined examination protocol and, from the blood flow behavior data, an individual impulse response function for the patient is determined. The blood flow behavior data can be gathered in the context of an imaging measurement of, for example, a prior CT measurement, in particular CTA, using a suitable contrast medium as in the later examination. This can relate to a "real" earlier contrast medium-assisted examination. In general, however, this is a special test measurement which is carried out with only a small quantity of contrast medium (the "test bolus"). The blood flow behavior data can however also be determined by other means, for example, optically with a test bolus in the form of a means for dye-marking the blood flow behavior, as described by F. Eisa et al. in "Optical tracking of contrast medium bolus to optimize bolus shape and timing in dynamic computed tomography", Physics in Medicine and Biology 2012, 57, pages N173 to N182, the entire contents of which are hereby incorporated by reference. The examination protocol includes, for example, the defined injection protocol for the administration of the contrast medium or test bolus.

a pre-measured heart rate signal associated with the pre-measurement is also detected. The formulation "associated with the pre-measurement" should be understood in this context as meaning that, depending on the available technical possibilities and the precise embodiment of the invention, the pre-measured heart rate signal represents, in a sufficient manner, the existing heart rate of the patient at a time point of the pre-measurement or during the pre-measurement. For example, the pre-measured heart rate signal can be detected in the context of the pre-measurement, i.e. during the pre-measurement or shortly therebefore or thereafter.

A device according to at least one embodiment of the invention for the automatic prediction of a likely contrast medium behavior for a contrast medium-assisted examination of an object under investigation comprises at least the following components:

an input interface for the detection of patient-specific blood flow behavior data in a pre-measurement making use of a defined examination protocol. The interface can be, for example, an interface to a memory store in which the relevant data are stored, but also an interface to an evaluating unit in which the measurement data from a test bolus measurement are currently being evaluated and from which the data can be taken up directly.

an impulse response function determining unit for determining an individual impulse response function based on the blood flow behavior.

an input interface for detecting a heart rate signal. This can also be, for example, an interface to a memory store or an interface to a measuring device for measuring and/or recording the heart rate signal, for example, an interface to an ECG. In principle, the input interfaces can be configured to detect the patient-specific blood flow behavior data and to detect a heart rate signal as well as being configured as a shared interface if the data and signals are stored together.

a calculation unit for the prediction of the likely contrast medium behavior based on the individual impulse response function, a pre-measured heart rate signal associated with the pre-measurement (the pre-measured heart rate signal being used again directly or—if the pre-measured heart rate signal has already been entered into the individual impulse response function—indirectly) as well as a current examination protocol and a currently detected heart rate signal.

BRIEF DESCRIPTION OF THE DRAWINGS

The invention will now be described in greater detail by reference to example embodiments illustrated in the drawings, in which.

DETAILED DESCRIPTION OF THE EXAMPLE EMBODIMENTS

Figure 1:
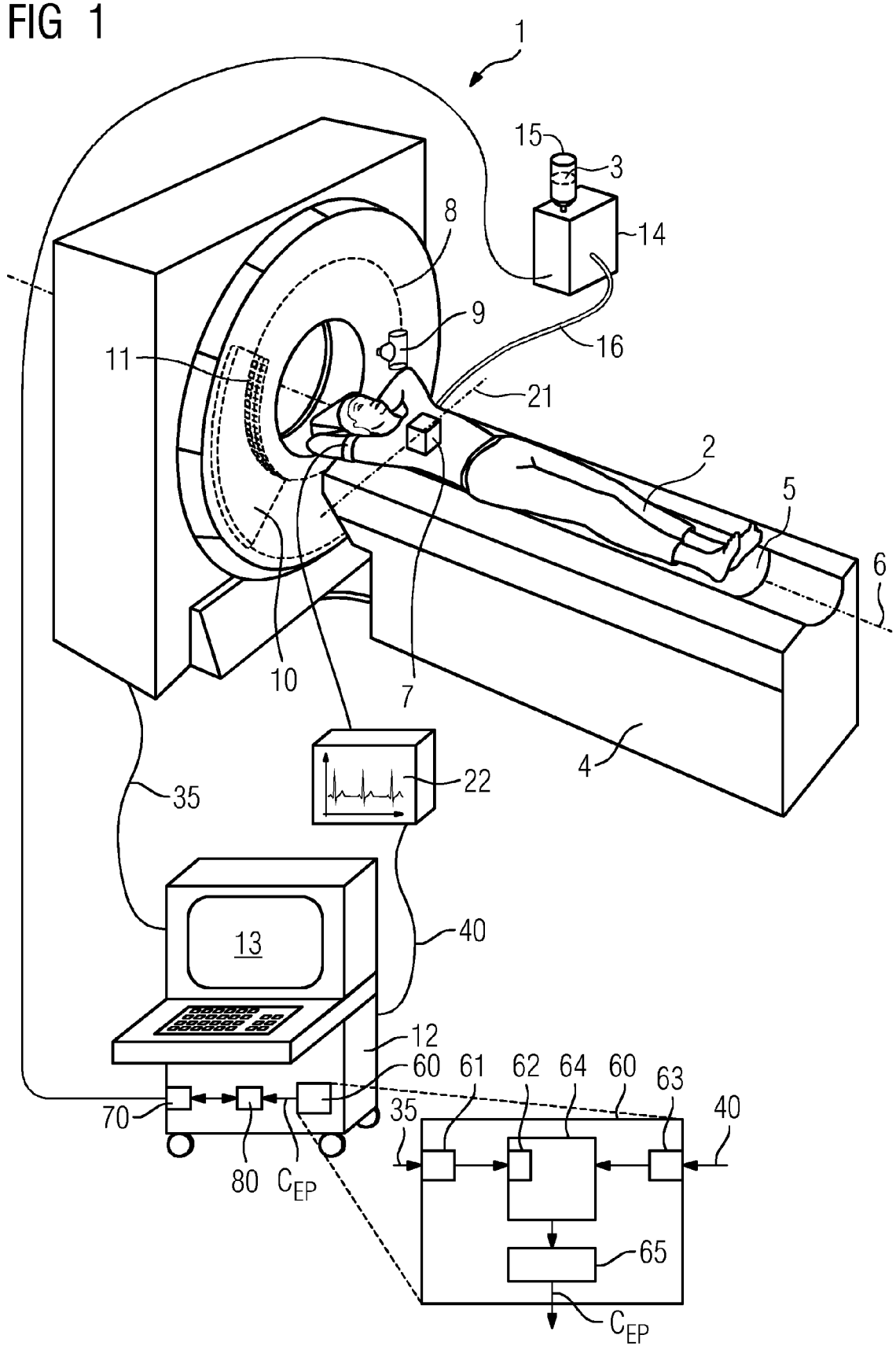
FIG. 1 is a perspective schematic representation of an imaging system according to an embodiment of the invention which is suitable for carrying out an angiographic examination method according to an embodiment of the invention for examining a patient using a contrast medium.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the method according to at least one embodiment of the invention, in order to predict a likely contrast medium behavior for a contrast medium-assisted examination of an object under investigation (hereinafter known, without restricting the generality thereof, as the "patient", for which reason the expression "patient-specific" is also used instead of the expression "investigation object-specific"), at least the following is carried out:

firstly, in a pre-measurement, patient-specific blood flow behavior data are determined using a defined examination protocol and, from the blood flow behavior data, an individual impulse response function for the patient is determined. The blood flow behavior data can be gathered in the context of an imaging measurement of, for example, a prior CT measurement, in particular CTA, using a suitable contrast medium as in the later examination. This can relate to a "real" earlier contrast medium-assisted examination. In general, however, this is a special test measurement which is carried out with only a small quantity of contrast medium (the "test bolus"). The blood flow behavior data can however also be determined by other means, for example, optically with a test bolus in the form of a means for dye-marking the blood flow behavior, as described by F. Eisa et al. in "Optical tracking of contrast medium bolus to optimize bolus shape and timing in dynamic computed tomography", Physics in Medicine and Biology 2012, 57, pages N173 to N182, the entire contents of which are hereby incorporated by reference. The examination protocol includes, for example, the defined injection protocol for the administration of the contrast medium or test bolus.

a pre-measured heart rate signal associated with the pre-measurement is also detected. The formulation "associated with the pre-measurement" should be understood in this context as meaning that, depending on the available technical possibilities and the precise embodiment of the invention, the pre-measured heart rate signal represents, in a sufficient manner, the existing heart rate of the patient at a time point of the pre-measurement or during the pre-measurement. For example, the pre-measured heart rate signal can be detected in the context of the pre-measurement, i.e. during the pre-measurement or shortly therebefore or thereafter.

the prediction of the likely contrast medium behavior is then made based on the individual impulse response function of the pre-measured heart rate signal (directly or—if the pre-measured heart rate signal has already been entered into the individual impulse response function—indirectly) and a current examination protocol and a currently detected heart rate signal. The currently detected heart rate signal represents the heart rate or heartbeat of the patient at the time of the later measurement for which the contrast medium behavior is to be predicted. For example, the signal can be detected at a sufficiently short interval before, or during, the examination. It should be expressly noted at this point that a contrast medium behavior prediction also covers the case that during the later examination of, for example, the CTA, the prediction of how the contrast medium spreads in the blood circulation is made from heartbeat to heartbeat in a type of "online preview". This is described in detail below.

Detection of the pre-measured heart rate signal and of the heart rate signal can relate both to each individual heartbeat (HB) if, for example, the heart rate is measured and recorded with an ECG, and to information relating to a mean heart rate (HR). The latter can be the case, for example, with pulse measuring devices which output the heart rate as a number of beats per minute (bpm).

Using the heart rate information or the heartbeat information during the pre-measurement, the patient function can be formulated to take account explicitly of the heart rate at the time point of the pre-measurement. Subsequently, in the event of a change in the heart rate, the contrast medium behavior can be better predicted at a later time point. The detection and recording and/or storage of the pre-measured heart rate signal and the detection of the current heart rate signal usually results in a significantly improved prediction of a likely contrast medium behavior for non-constant heart rates.

In addition, a process of this type can preferably be used in a method according to at least one embodiment of the invention for automatic activation of a medical imaging system, wherein a reference time point—for example, a start time point for starting an image acquisition in a particular region—is determined for the imaging system based on a start time point of the administration of the contrast medium and the predicted contrast medium behavior. For example, a delay time can arise between the start of the contrast medium administration and a start of the scanning by the imaging system from the position of a local maximum of a predicted contrast medium behavior.

The determination of a reference time point of this type can also be useful for other processes, for example, a later evaluation of image data sets of a contrast-medium recording. It is therefore important in many cases to know at what phase particular images were recorded, for example, whether it was a phase when the contrast medium was first distributed or accumulated in a particular structure or whether the images were generated in a phase in which the contrast medium disappears again, that is, is removed from the structure.

A device according to at least one embodiment of the invention for the automatic prediction of a likely contrast medium behavior for a contrast medium-assisted examination of an object under investigation comprises at least the following components:

- an input interface for the detection of patient-specific blood flow behavior data in a pre-measurement making use of a defined examination protocol. The interface can be, for example, an interface to a memory store in which the relevant data are stored, but also an interface to an evaluating unit in which the measurement data from a test bolus measurement are currently being evaluated and from which the data can be taken up directly.
- an impulse response function determining unit for determining an individual impulse response function based on the blood flow behavior.
- an input interface for detecting a heart rate signal. This can also be, for example, an interface to a memory store or an interface to a measuring device for measuring and/or recording the heart rate signal, for example, an interface to an ECG. In principle, the input interfaces can be configured to detect the patient-specific blood flow behavior data and to detect a heart rate signal as well as being configured as a shared interface if the data and signals are stored together.
- a calculation unit for the prediction of the likely contrast medium behavior based on the individual impulse response function, a pre-measured heart rate signal associated with the pre-measurement (the pre-measured heart rate signal being used again directly or—if the pre-measured heart rate signal has already been entered into the individual impulse response function—indirectly) as well as a current examination protocol and a currently detected heart rate signal.

The contrast medium behavior prediction or a suitable function or table which represents the contrast medium behavior to be expected can then be output via an output interface of the device according to at least one embodiment of the invention, for example, to other units which further process the contrast medium behavior prediction and, in particular, carry out or store further calculations.

A device of this type for automated prediction of the likely contrast medium behavior is particularly preferably configured as part of a control device for an imaging system. This means that the control device itself comprises this device for automated prediction of the likely contrast medium behavior. In this case, the control device preferably also comprises an interface for the detection or output of a contrast medium administration start time point and a reference time point determination device for determining a reference time point for the imaging system based on the contrast medium administration start time point and on the likely contrast medium behavior. This has the advantage that the control device can determine the contrast medium behavior prediction entirely automatically and directly, based on the pre-measurement and that the imaging system can later be controlled accordingly with the aid of this control system such that during the actual measurement, the image data acquisition can be begun at the right time point following the contrast medium administration and/or the image data can be chronologically linked to the reference time point, and stored.

In principle, however, a device according to at least one embodiment of the invention can also be used for automatic prediction of a likely contrast medium behavior on other computers which, for example, accept the necessary blood flow behavior data from other components and are connected, for example, to the imaging system via a network. This is particularly useful if more computationally intensive tasks are to be reallocated out of the control device in order to make the computational capacity of the control system fully available for controlling other measurements.

An imaging system according to at least one embodiment of the invention for generating image data from the interior of an object under investigation preferably comprises a control device as described above, which also has a device according to at least one embodiment of the invention for automatic prediction of a likely contrast medium behavior.

In particular, the impulse response function determining device and the calculation unit of the device according to at least one embodiment of the invention for automated prediction of a likely contrast medium behavior can each be realized as software modules on a suitable computer with the relevant storage capability. The input interfaces and the output interface can also be realized in the form of pure software, provided only one transfer of the blood flow behavior data and/or one output of the contrast medium behavior prediction from and/or to other further units or memory stores—particularly where realized on the same computer unit—is necessary. These interfaces can essentially also be realized as combined hardware/software interfaces in order to realize an external input and output, for example, hardware interfaces specifically configured with the aid of software components. A realization largely through software has the advantage that, for example, previously used control devices for imaging systems can be reconfigured by easy means with a software update in order to operate in the manner according to an embodiment of the invention. The object is therefore also achieved with a computer program product which can be loaded directly into a memory store of a programmable control device having program portions in order to carry out all the steps of the method according to an embodiment of the invention when the program is executed in the control device.

The dependent claims each contain particularly advantageous developments and embodiments of the invention, wherein the claims of one category can also be further developed in accordance with the dependent claims of another category.

Depending on the heart rate information, that is, the type of detection or recording of the heart rate signal and/or the implementation of the CEP algorithms, one or more possibilities exist for optimizing the prediction of the contrast medium behavior for varying heart rates.

In a preferred variant, based on the pre-measured heart rate signal, a heartbeat-related impulse response function is determined. This individual "heartbeat-related impulse response function" defines the individual impulse response function dependent on the heartbeat count. In other words, whereas the above-described and conventionally commonplace individual impulse response function (also sometimes referred to explicitly hereinafter, for differentiation, as the "time-related impulse response function") is considered in the time domain, i.e. as a function over time t, a "heartbeat-related" impulse response function is considered in the "heart rate domain" or the "heartbeat domain", i.e. what is under consideration here is a function over heartbeat count, which is known hereinafter by the abbreviation HB (heartbeat).

To this end, it is possible to determine the patient-specific blood flow behavior data and the examination protocol, respectively, in the heartbeat domain. For example, the data can be recorded directly as dependent on a heartbeat which is determined in parallel. The examination protocol could also be pre-determined depending on the heartbeat count or could be processed controlled by the heartbeat. However, it is also possible initially to detect all the data in the time domain and then to convert said data into the heartbeat domain.

Similarly to equation [1], in the heartbeat domain the following applies $$C(HB) = IF(HB) \otimes AIR(HB) \quad [2]$$

wherein, as stated above, (HB) here signifies the dependence on the heartbeat. The heartbeat-related impulse response function or patient function AIR(HB) can therefore also be determined mathematically by a deconvolution, given patient-specific blood flow behavior data C(HB), i.e. the contrast medium accumulation in the patient, depending on the heartbeat, and the known injection protocol IF(HB).

However, since a plurality of standard programs is already available for the deconvolution in the time domain or the frequency domain, it can be more advantageous with regard to the total effort, firstly to determine a time-related individual impulse response function $AIR_{TB}(t)$ in the usual manner and to convert said response function into a heartbeat-related impulse response function $AIR_{TB}(HB)$ using the pre-measured heart rate signal. This is made possible with, for example, the following equation:

$$AIR_{TB}(HB) = AIR_{TB}(t \cdot HR_{TB}) \quad [3]$$

where $HR_{TB}$ is the heart rate determined at the pre-measurement. The abbreviation "TB" (test bolus) is, in general, used below to indicate that data involved come from the pre-measurement, regardless of whether a test bolus has been utilized. This means that $AIR_{TB}$ is the individual impulse response function being sought, which has been determined on the basis of data from the pre-measurement.

As mentioned above, the heart rate can be calculated or determined differently. Frequently, what is being considered is a mean heart rate which is found from the number of heartbeats in a defined time period. It is herein possible to define the time period over all the previous heartbeats since the measurement of the heart rate and to divide the number of measured heartbeats by this time. It is also possible to form a type of sliding mean value which extends over a particular time period or a particular number of elapsed heartbeats (for example, the last ten heartbeats). A sliding mean value formation of this type is implicitly carried out, for example, with a typical pulse measurement taken using a simple pulse meter. In an extreme case, a completely current heart rate can only be based on the last heartbeat in that simply the inverse value of the time interval between the last and the previous heartbeat is used as the heart rate.

If it is not the same time unit that is used to determine the heart rate $HR_{TB}$ as for determining the time t, a conversion factor U must also be used in equation [3]:

$$AIR_{TB}(HB) = AIR_{TB}\left(t \cdot \frac{HR_{TB}}{U}\right) \quad [3']$$

If the time t is typically measured in the unit of seconds (s) as usual, and the heart rate in heartbeats per minute (bpm; beats per minute), the conversion factor is U=60, i.e. the following equation applies:

$$AIR_{TB}(HB) = AIR_{TB}\left(t \cdot \frac{HR_{TB}}{60}\right) \quad [3'']$$

If the individual heartbeat-related impulse response function $AIR_{TB}(HB)$ is known and if, in the later contrast medium-assisted measurement for the actual examination, the examination protocol, in particular the injection protocol $IF_{CTA}(HB)$ is also controlled in the heartbeat domain or converted into the heartbeat domain (a possible method for said conversion will be is described later), the contrast medium behavior prediction $C_{EP}(HB)$ can be directly determined without difficulty using the following equation (see equation [1]) using the typical convolution operation:

$$C_{EP}(HB) = IF_{CTA}(HB) \otimes AIR_{TB}(HB) \quad [4]$$

Ultimately, the function $C_{EP}(HB)$ defines the heartbeat-related contrast medium behavior prediction, that is, an expected contrast medium accumulation at a particular position in the patient depending on the heartbeat. The abbreviation "EP" stands for the prediction of enhancement (Enhancement Prediction). Furthermore, for general clarification, the abbreviation "CTA" is used to indicate that the data concerned are from the later contrast medium-assisted measurement for which the contrast medium behavior is to be predicted, specifically independently of whether this is actually a CTA examination or another contrast medium-assisted examination.

The use of equation [4] is particularly advantageous if, during the later contrast medium-assisted measurement, the heart rate signal is detected and processed in a manner involving heartbeat-by-heartbeat observation in order to use the prediction effectively.

However, where during the later contrast medium-assisted measurement, operation does not take place in the heartbeat domain, the following alternative preferred variant of the method according to at least one embodiment of the invention suggests itself. Herein, based, for example, on a heart rate signal that is currently detected (shortly before or during the main scan, i.e. the actual measurement) and on the heartbeat-related impulse response function, a time-related corrected individual impulse response function is formed. Alternatively, a time-related corrected individual impulse response function of this type can be determined directly from the time-related individual impulse response function. In both cases, the prediction of the likely contrast medium behavior $C_{EP}(t)$ takes place in the time domain by combining the corrected time-related impulse response function $\text{AIR}_{CORR}(t)$ with the current examination protocol or injection protocol (also related in the usual manner to the time) $\text{IF}_{CTA}(t)$ in accordance with $$C_{EP}(t) = \text{IF}_{CTA}(t) \otimes \text{AIR}_{CORR}(t) \quad [5]$$

Therefore, in these variants, for the examination of the patient using a contrast medium, a correction of a patient-specific arterial contrast medium impulse response function is carried out for non-constant heart rates for improved prediction of the likely contrast medium behavior. Thus, in one variant, data which represent the heartbeat signal and the blood flow behavior data can be fed in advantageous manner to a CEP algorithm which calculates the individual impulse response function from these values. Then, the corrected individual impulse response function is derived from this individual impulse response function and a CTA heart rate determined shortly before the actual examination. Alternatively, the corrected individual impulse response function can be calculated from a time-related impulse response function which is initially conventionally determined using data which represent the heart rate signal during the pre-measurement, and from the data which represent a heart rate signal determined shortly before the actual contrast medium-assisted examination, as the parameters required for the examination that is to be carried out.

When, initially, an individual heartbeat-related impulse response function $\text{AIR}_{TB}(HB)$ has been determined, the corrected individual impulse response function can be calculated therefrom by scaling the individual heartbeat-related impulse response function with a time scaling factor which is given by the inverse value of a heart rate $\text{HR}_{CTA}$ determined from the currently detected heart rate signal:

$$\text{AIR}_{CORR}(t) = \text{AIR}_{TB}(HB/\text{HR}_{CTA}) \quad [6]$$

If the time t itself and the heart rate are determined with different time units, a conversion factor U can again be used:

$$\text{AIR}_{CORR}(t) = \text{AIR}_{TB}(HB/(\text{HR}_{CTA}/U)) = \text{AIR}_{TB}(HB/\text{HR}_{CTA} \cdot U) \quad [6']$$

wherein given the usual units (firstly s and secondly bpm) U=60, as has already been described in relation to equation [3].

If, however, only one individual impulse response function $\text{AIR}_{TB}(t)$ has been determined as usual in the time domain, the corrected individual impulse response function can be calculated therefrom by scaling the individual time-related impulse response function with a time scaling factor which is given by a heart rate $\text{HR}_{TB}$ determined from the pre-measured heart rate signal in relation to a heart rate $\text{HR}_{CTA}$ determined from the currently detected heart rate signal:

$$\text{AIR}_{CORR}(t) = \text{AIR}_{TB}(t \cdot \text{HR}_{TB}/\text{HR}_{CTA}) \quad [7]$$

In all the equations [6] to [7], the heart rate can be a mean heart rate as described above or a heart rate relating to just one heartbeat.

However, in the above equations [6] to [7], the fact that the change in heart rate also ultimately has the result that, with an injection protocol which is unchanged in relation to the time domain, different quantities of contrast medium are administered per heartbeat has not yet been taken into account. In other words, a change in the heart rate leads to a change in the injection protocol in the heartbeat domain. In order to take this into account and to improve the prediction further, in each of the above equations [6] to [7], a correction factor can be included which compensates for said change. Therefore, in order to form the corrected individual impulse response function, the scaled individual impulse response function is multiplied by the inverse of the respective time scaling factor. For equation [6], the following then results $$\text{AIR}_{CORR}(t) = (\text{HR}_{CTA}) \cdot \text{AIR}_{TB}(HB/\text{HR}_{CTA}) \quad [6a]$$

and for equations [6'] and [7], accordingly:

$$\text{AIR}_{CORR}(t) = (\text{HR}_{CTA}/U) \cdot \text{AIR}_{TB}(HB/\text{HR}_{CTA} \cdot U) \quad [6'a]$$

$$\text{AIR}_{CORR}(t) = (\text{HR}_{CTA}/\text{HR}_{TB}) \cdot \text{AIR}_{TB}(t \cdot \text{HR}_{TB}/\text{HR}_{CTA}) \quad [7a]$$

Graphically represented, this correction factor ($\text{HR}_{CTA}$), ($\text{HR}_{CTA}/U$) or ($\text{HR}_{CTA}/\text{HR}_{TB}$) or prefactor in the associated equations provides that when adapting the AIR curve over the width, the amplitude of the individual impulse response function AIR changes reciprocally so that the area under the AIR curve remains constant.

If, for example, equation [7a] is inserted into equation [5], the prediction of the likely contrast medium behavior $C_{EP}(t)$ based on the usual time-related individual impulse response function $\text{AIR}_{TB}(t)$ and the heart rate $\text{HR}_{TB}$ during the pre-measurement and the current heart rate $\text{HR}_{CTA}$ during the later measurement, is given as follows:

$$C_{EP}(t) = \text{IF}_{CTA}(t) \otimes (\text{HR}_{CTA}/\text{HR}_{TB}) \cdot \text{AIR}_{TB}(t \cdot \text{HR}_{TB}/\text{HR}_{CTA}) \quad [8]$$

For the other methods in accordance with equations [6] and [6'], the calculation takes place similarly.

Alternatively, the correction factor ($\text{HR}_{CTA}/\text{HR}_{TB}$), which takes account of the heart rate-dependency of the examination protocol, can also be multiplied by the examination protocol or the injection protocol $\text{IF}_{CTA}(t)$:

$$C_{EP}(t) = (\text{HR}_{CTA}/\text{HR}_{TB}) \cdot \text{IF}_{CTA}(t) \otimes \text{AIR}_{TB}(t \cdot \text{HR}_{TB}/\text{HR}_{CTA}) \quad [9]$$

Since, for the convolution operation generally, $$a \cdot (f \otimes g) = (a \cdot f) \otimes g = f \otimes (a \cdot g) \quad [10]$$

applies, this leads to the same result. Equation [9] gives an example of the calculation variant with equation [7]. But this applies equally for the variants with equations [6] and [6'].

As mentioned above, the pre-measured heart rate signal can be detected in different ways. It is only necessary that the heart rate is represented in an adequate manner during the pre-measurement. In order to enable the most precise correction possible, the blood flow behavior data and the pre-measured heart rate signal are preferably correlated temporally, i.e. detected and recorded in parallel temporally. Particularly preferably, the detection of the pre-measured heart rate signal is carried out by parallel recording of ECG data during the pre-measurement.

Depending on the implementation, a mean heart rate can be derived from the ECG data during the pre-measurement if, for example, during the later measurement, no ECG is available, but nevertheless processing can only take place with the mean heart rate. This simplifies the calculations since, for example, in accordance with the above equations [7] or [7a], a correction of the individual impulse response function or in accordance with equations [8] or [9], a correction of the contrast medium behavior prediction is carried out.

In the following examples, for the sake of simplicity and without limitation of the scope, it is taken that the pre-measurement involves a test bolus measurement and the actual contrast medium-assisted examination is a CTA.

FIG. 1 shows a medical imaging system (diagnostic device), in this example, a computed tomography scanner 1, which is suitable for carrying out the examination method according to an embodiment of the invention for examining a patient 2 using a contrast medium 3. In place of the above-mentioned computed tomography scanner 1, a magnetic resonance device or ultrasonic tomography scanner can also be used.

A patient support table 4 with a movable table panel 5 on which the patient 2 can be supported is associated with the computed tomography scanner 1. The table panel 5 is displaceable in the direction of a rotation axis 6 such that an examination region 7 associated with the patient 2 can be moved through an opening of a gantry 8 of the computed tomography scanner 1 into the measuring region of a recording system 9, 10. The patient 2 and the recording system 9, 10 are displaceable in this way relative to one another in the direction of the rotation axis 6 such that different scanning positions can be assumed. The examination region 7 can be, for example, the heart of the patient.

In order to detect projections, the recording system 9, 10 has an X-ray emitter 9 in the form of an X-ray tube and an X-ray detector 10 arranged opposed thereto, wherein the X-ray detector 10 is configured arc-shaped and comprises a plurality of detector elements 11 arrayed in detector rows. The X-ray emitter 9 generates radiation in the form of a fan-shaped X-ray beam which penetrates the measuring region and then impinges upon the detector elements 11 of the X-ray detector 10. The detector elements 11 generate an attenuation value dependent on the attenuation of the X-ray radiation passing through the measuring region. The conversion of the X-ray radiation into an attenuation value is carried out, for example, by way of a photodiode which is optically coupled to a scintillator or by way of a direct-conversion semiconductor. In this way, the X-ray detector 11 generates a set of attenuation values which is referred to as a projection.

The recording system 9, 10 is rotatably arranged at the gantry 8 such that projections can be detected from different projection directions. Depending on the operating mode that has been set for the computed tomography scanner 1, the scanning is carried out with a fixed or changing projection direction with a simultaneously fixed or changing scanning position. By rotating the gantry 8 while simultaneously and continuously advancing the patient 2 in the direction of the rotation axis 6, for example, projections are detected from a plurality of different projection directions at different positions along the rotation axis 6 or along the patient 2. The projections obtained in this way by the recording system 9, 10, by way of spiral scanning—rotation of the recording system 9, 10 and simultaneous advancing of the table panel 5—are transferred to a computer unit or control device 12 of the imaging system 1 and are reconstructed into image data which can be output on a display 13. The image data can comprise, for example, one or more sectional views or 3-dimensional views of the examination region 7.

For the examination of blood-perfused organs, for example a heart, a liver or a vessel, in order to enhance the visible contrast in relation to the surrounding soft tissues, a contrast medium 3 can be injected into the patient 2 by way of a contrast medium injector 14. The contrast medium 3 is pumped into a vein of the patient 2 in an automated manner—pre-defined by an injection protocol—typically time-regulated, from a supply container 15 via a contrast medium hose 16 in a settable quantity and at a settable flow rate. Control commands for contrast medium administration and injection protocols can be transferred via an electrical connection between the computer unit 12 and the contrast medium injector 14.

As the contrast medium 3 spreads out in the interior of the body, the contrast medium 3 introduced passes through the blood circulation of the patient 2 and only reaches the examination region 7 after a certain time. In order to be able to determine this previously unknown delay between the start of the injection and the start of the contrast medium accumulation, before the main scan (CTA), a small quantity of contrast medium, known as the "test bolus", can be injected. On reaching the examination region 7, the concentration of the contrast medium 3 of the test bolus in the blood initially increases, passes through a maximum 18 and subsequently falls again. The temporal behavior of the concentration can be depicted in the form of a contrast medium behavior 25 over time 20, which is essentially represented by the test bolus signal 19. In clinical routine, based on this test bolus signal 19 or on a contrast medium prediction derived therefrom, suitable operating parameters of the computed tomography scanner 1 are determined, such that the main scan is carried out at a time point and a speed at which the concentration of the contrast medium 3 in the examination region 7 is as great as possible. The operating parameters comprise, for example, the start time point of the scanning and the scanning speed and/or the pitch value, that is, the ratio between the advancing of the table panel 5 per rotation of the gantry 8 and the slice thickness of the X-ray detector 10.

In the example embodiment shown, the control device 12 is equipped with a device 60 according to the invention for predicting a likely contrast medium behavior $C_{EP}$ which will be described in greater detail below. In addition, the control device 12 comprises an interface 70 for the detection or output of a contrast medium administration start time point and a reference time point determination device 80, which then determines a reference time point for the imaging system taking account of the contrast medium administration start time point and based on the likely contrast medium behavior $C_{EP}$, so that, for example, shortly before a likely time point of the maximum contrast medium accumulation in the region under examination, an imaging measurement is automatically started for this region with the appropriate further parameters.

Figure 2:
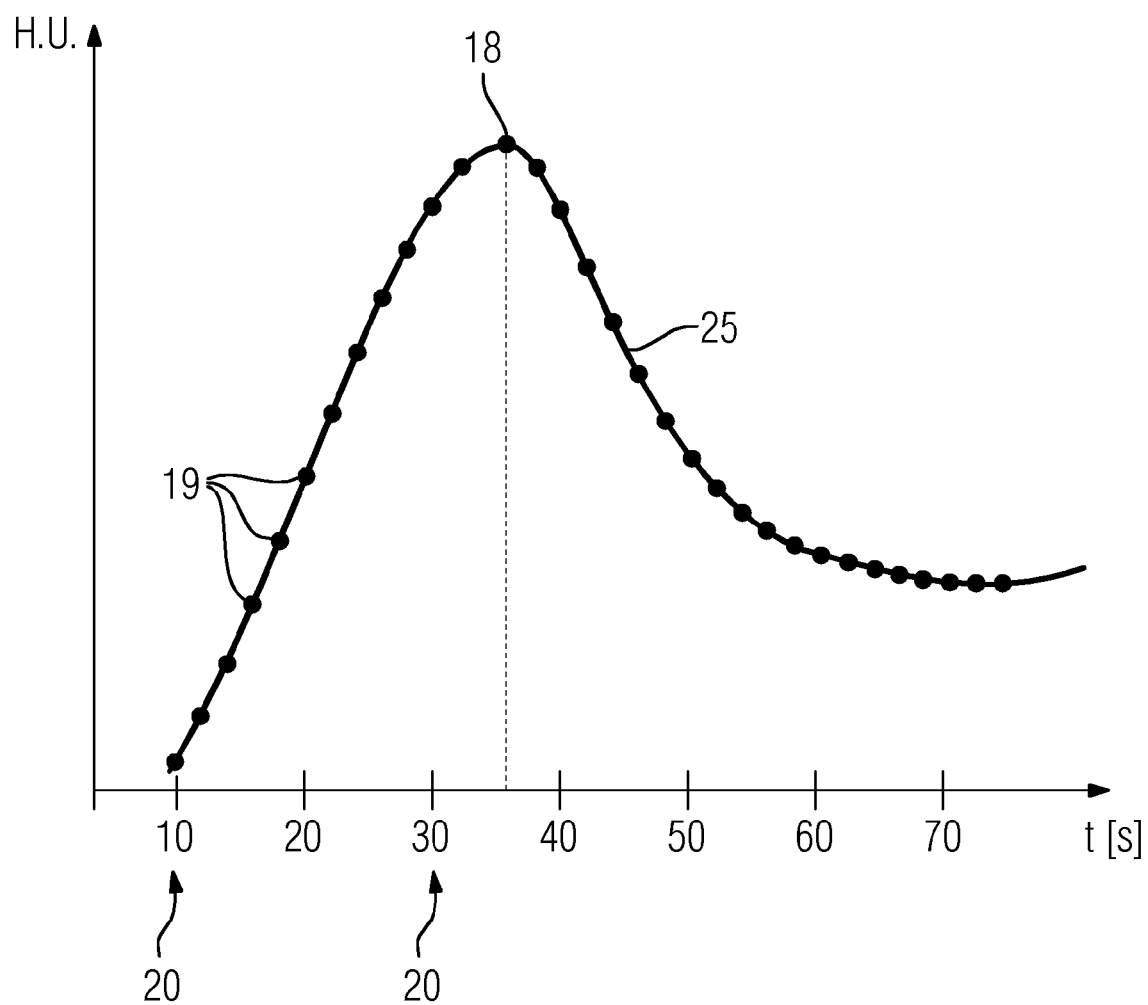
FIG. 2 is a contrast medium curve determined during a preexamination.

A typical contrast medium behavior 25 of a test bolus is shown by way of example in FIG. 2. The time t is represented in units of seconds (s) along the x-axis. The y-axis represents the relative attenuation values in Hounsfield units (HU). In the example, attenuation values 19 have been detected every two seconds at scanning time points 20. For reasons of clarity, not all the attenuation values 19 and not all the scanning time points 20 have been provided with a reference sign. The attenuation values 19 have been entered as points on the graph and can be used to calculate a patient-specific impulse response function (AIR).

In order to determine the contrast medium behavior 25 of a test bolus in the context of a pre-measurement, at least the following are carried out:

setting a fixed scanning position 21, preferably in the examination region (see FIG. 1), carrying out a series of scans at pre-defined scanning time points 20 to determine the contrast medium behavior, wherein at each sampling time point 20, a CT attenuation value 19 is detected, by which a concentration of the contrast medium 3 at the scanning position 21 is represented, and storing the CT attenuation values 19 of the contrast medium behavior and the scanning time points 20 in order to calculate parameters and predictions for later examinations of the patient 2.

Figure 3:
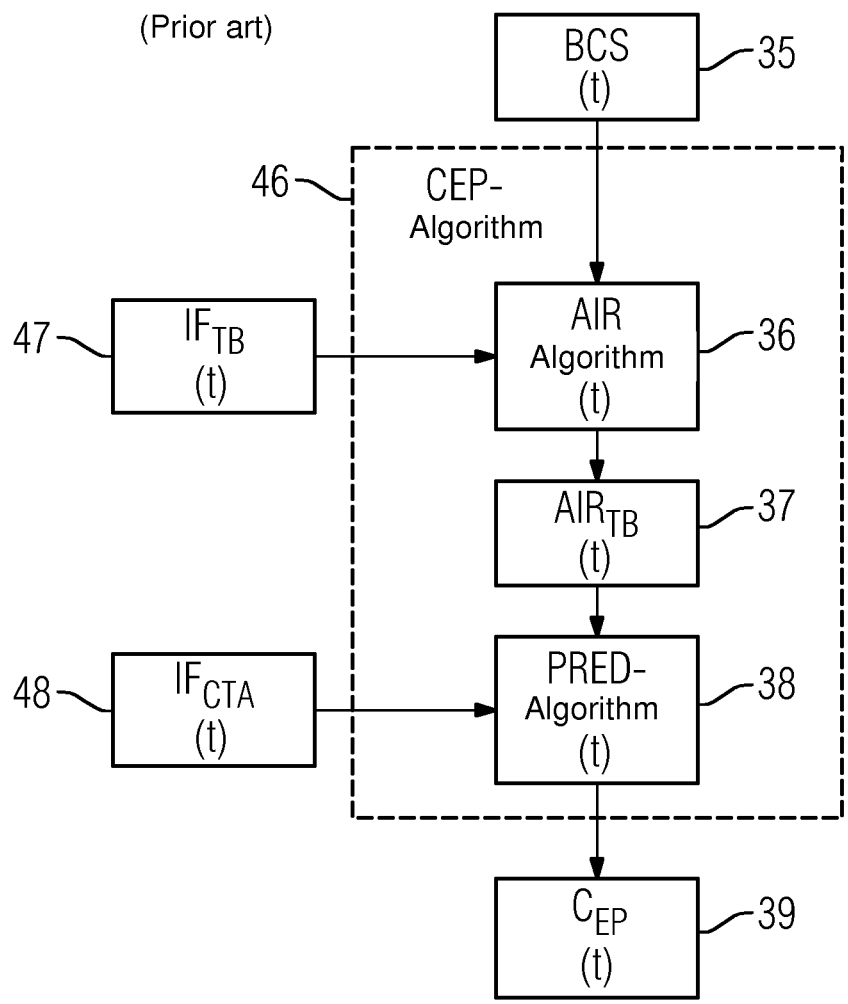
FIG. 3 is a known method according to the prior art for predicting the contrast medium behavior in the time domain.

FIG. 3 shows a known calculation method for predicting the contrast medium behavior according to the prior art. From the blood flow behavior data 35, referred to below as the "blood circulation signal" 35 (BCS(t)), which are determined, for example, in the pre-measurement from the test bolus TB or optically, and from a defined examination protocol 47, specifically the injection protocol $IF_{TB}(t)$ used during the pre-measurement, using an AIR algorithm 36, the individual patient function 37 ($AIR_{TB}(t)$) is calculated. Using a PRED algorithm 38 and the contrast injection protocol 48 of the main scan $IF_{CTA}(t)$, a prediction 39 ($C_{EP}(t)$) of the contrast medium behavior of the main scan is calculated. The different calculations of the CEP algorithm 46, for example, with the method disclosed in the older application DE 10 2012 209 410.5, the entire contents of which are hereby incorporated herein by reference, are always carried out in the time domain and/or the Fourier domain derived from the time domain.

It should be noted here that the blood flow behavior data BCS(t) (where measured with the contrast medium test bolus) and the contrast medium behavior prediction $C_{EP}(t)$ concern essentially similar data, specifically a function of the CT attenuation values which represent the contrast medium accumulation at a particular point within the examination region, as a function of time.

In all previous approaches, in order to make a prediction concerning the contrast medium accumulation in the patient based on a test bolus measurement, the heart rate of the patient was assumed to be constant. However, since the blood circulation and thus the flow rate of the contrast medium depend on the heart rate, the prediction described below wherein heart rate information is taken into account and is included in the calculations, is potentially better or should be better. This applies, above all, in patients with irregular heart rates, at least over relatively long time intervals.

Figure 4:
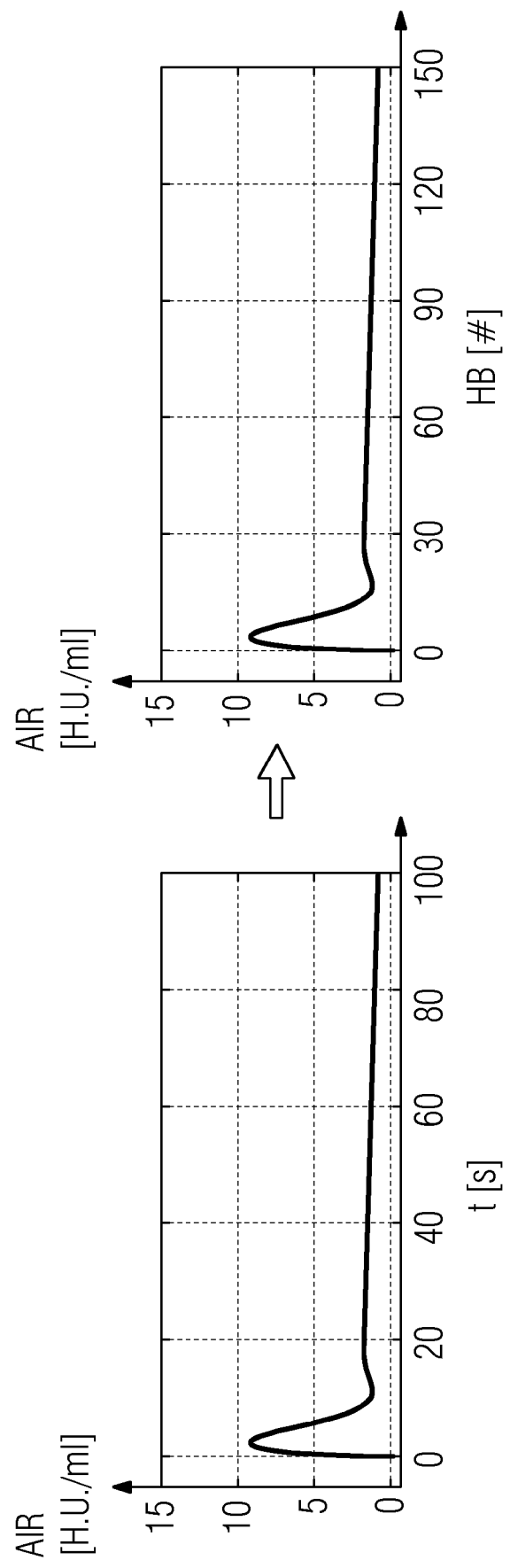
FIG. 4 is a graphical representation to illustrate the conversion according to an embodiment of the invention of the derived patient function $AIR_{TB}(t)$ as a function of time into a function $AIR_{TB}(HB)$ of the number of heartbeats.

By determining the heart rate with a pulse measuring device or an ECG device 22 during a test bolus measurement, the individual patient function (AIR—Arterial Impulse Response—patient-specific arterial contrast medium impulse response function) can be converted into a patient function which is directly dependent on the heartbeat count and is therefore effectively "independent" of the heart rate. Otherwise expressed, the time axis becomes an axis which shows the number of heartbeats. This is shown graphically with an example where a regular heart rate of 90 beats per minute (bpm) is assumed in FIG. 4 in which, in the graph at left, the individual patient function AIR(t) is shown over time and, in the graph at right, the individual patient function AIR (HB) is shown over the heart rate.

What is important is that this conversion of the time axis is in principle only possible when the heart rate has been measured for the test bolus measurement, preferably during the test bolus measurement. This conversion of the time axis can be carried out, to a first approximation, with the mean heart rate during the test bolus measurement. It would also be possible, rather than using the mean heart rate, to take each individual heartbeat into account if, for example, an ECG has been measured and registered from the start of the test bolus injection. It can also arise, depending on the implementation in question, that only the mean heart rate is able to be used in the CEP algorithm, although each individual heartbeat has been measured with the ECG during the test bolus.

Preferably, therefore, at the same time as the measurement for deriving an AIR, that is, the test bolus measurement, the heart rate is measured, for example, with a pulse measuring device or an ECG device 22 (see FIG. 1). Account is not taken in this way, nowadays, of the heart rate information and this is clearly also not possible for test bolus scans on known CT devices at present. Using this information concerning the heart rate, the patient function which has been estimated from the test bolus can be created regardless of an unstable or changing heart rate that was present at the time of the test bolus. Subsequently, the contrast medium behavior can be better predicted at a later time point should the heart rate have changed.

This has the following advantages:
1. Possible changes in the heart rate between the test bolus measurement and the CTA scan can be taken into account in the prediction of the contrast medium behavior in the patient during the CTA scan. Based on this prediction the scan start, for example, can be optimized.
2. Particularly for patients with an irregular heart rate, a better prediction of the contrast medium behavior is expected.
3. A patient function which is independent of the heart rate offers new possibilities for characterizing the cardiovascular status of a patient. This new biomarker could possibly be useful in patients who are receiving systemic chemotherapy or who suffer from a degenerative cardiovascular disease.
4. Since CTA scans of the heart are acquired ECG-triggered, the measurement of heart rate during the test bolus and the later measurement for these patients does not result in any extra costs or extra effort from the medical radiological assistants.
5. If a heartbeat-related impulse response function AIR(HB) has been determined, this can also be stored and later used not only for a main scan following a relatively short time later, but for any desired further examinations. A further test bolus scan can be dispensed with because the heartbeat-related impulse response function AIR(HB) can always be adapted to the current heart rate.
6. With the measurements of the pre-measured heart rate signal and of the current heart rate signal, the arrival time (bolus arrival time) can very easily be better predicted if the contrast medium only arrives at the measurement point after the start point of the injection. This is possible regardless of the further calculations or corrections of the curve shape of the impulse response function, i.e. the impulse response function is thereby merely displaced along the time axis.

Figure 5:
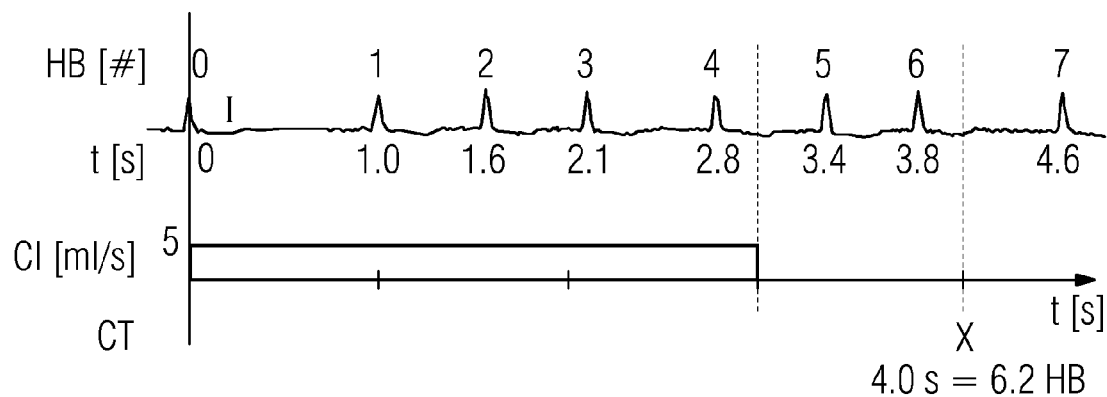
FIG. 5 is a graphical representation to explain the relationship between events in the time domain and the heartbeat domain.

FIG. 5 serves to illustrate the simultaneous acquisition of the heart rate information, according to an embodiment of the invention, and the pre-measurement in order to derive the individual AIR and shows the relationship between events in the time domain and in the heartbeat domain. In the upper line of FIG. 5, the ECG of a patient is shown over time t. For each individual heartbeat HB, it is known at what time point t said beat takes place. The lower line shows, by way of example, a contrast medium injection CI [ml/s] of a test bolus with a total contrast medium quantity of 15 ml at a rate of 5 ml/s (this curve belongs to a typical injection protocol for a test bolus). The injection time t[s] for the contrast medium of 3 s is equivalent to 4.3 heartbeats HB. The CT scan begins after 4 seconds, corresponding to 6.2 heartbeats HB. Similarly to these examples, the scanning time points 20 of the test bolus measurement 19 can also be converted from seconds to the number of heartbeats HB[#]. The test bolus measurement 19 is then obtained as a function of the number of heartbeats HB[#]. If the heart rate signal is recorded simultaneously, this relationship can be determined at any time retrospectively.

Figure 6:
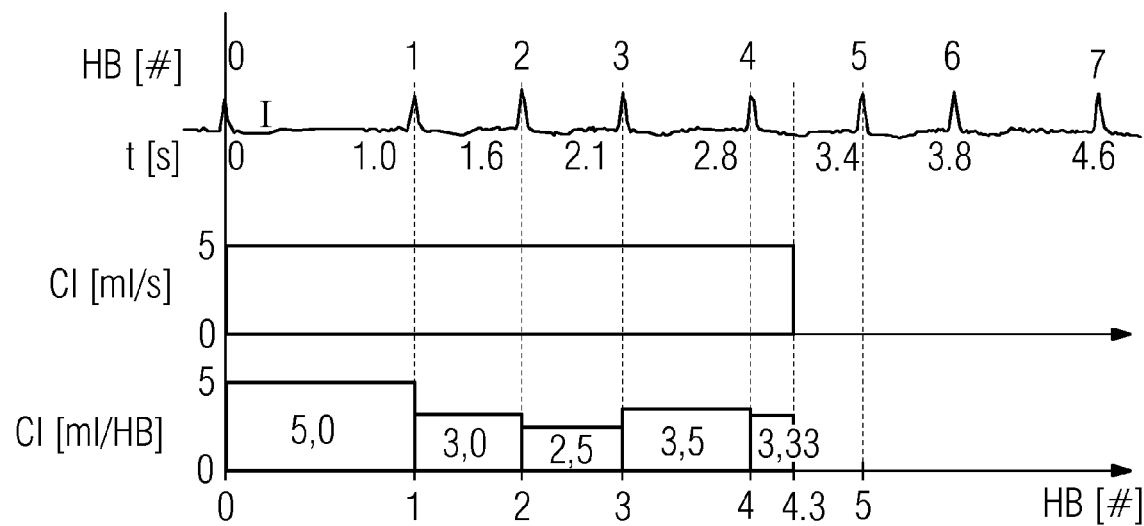
FIG. 6 is a graphical representation showing an injection protocol of a test bolus and ECG data as well as an injection protocol converted to a heart rate.

For proper use of the heart rate information in the prediction, not only should the time information be converted, but also possibly, depending on the implementation, the information of the examination protocol, in this example the injection protocol for the test bolus, should be amended. If, for example, an AIR algorithm which, as explained below, is able to calculate directly in the heartbeat domain, is used, the injection protocol can be transferred in advance from the time domain into the heartbeat domain. The injection protocol IF (CI in the figure) in [ml/s] can be converted, as shown in FIG. 6, into the units [ml/HB] if the analysis is carried out using each individual heartbeat. In the case of a contrast medium injection CI [ml/s] of a test bolus of 15 ml contrast medium at a rate of 5 ml/s, the resulting behavior of the contrast medium injection CI [ml/HB] is as shown. The flow rate in [ml/HB] is found simply by multiplying the time interval between two heartbeats [s] and the flow rate in [ml/s].

Figure 7:
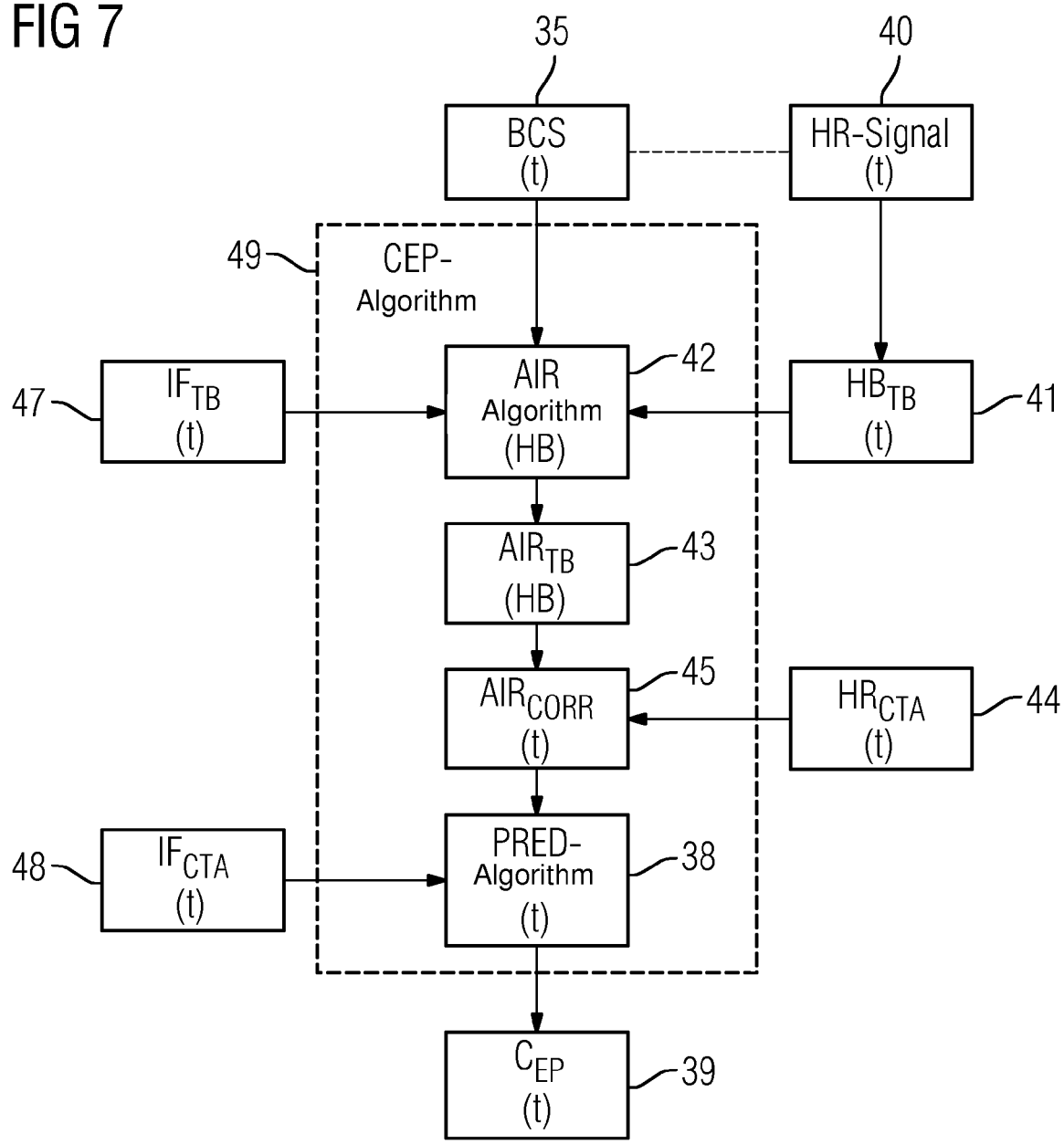
FIG. 7 is a graphical representation of a first embodiment of a method according to the invention for predicting the contrast medium behavior.

FIG. 7 shows a flow diagram for a first example of a method according to an embodiment of the invention, wherein the implementation of the AIR algorithm permits derivation of the individual patient-specific impulse response function or patient function AIR in the heartbeat domain (HB) rather than in the time domain (t), the HR signal is an ECG signal wherein each individual heartbeat can be taken into account, and the corrected prediction of the contrast medium behavior during the main scan is based on a mean heart rate ($HR_{CTA}(t)$) measured shortly before the main scan.

To this end, apart from the blood flow signal 35 (BCS), a heart rate signal 40 (HR-signal(t)) characterizing the heart rate, in this case an ECG, is determined and is also made use of and, as indicated by the dotted line, is time-correlated to the blood flow signal 35 and recorded.

From this heart rate signal 40, each individual heartbeat $HB_{TB}(t)$ during the test bolus administration is determined as a function of time, as illustrated in FIG. 5 with method step 41. The function $HB_{TB}(t)$ therefore also represents the number of heartbeats after a particular time t. The identification 41 of the individual heartbeats $HB_{TB}$ can take place, for example, according to international standards, as defined by The CSE Working Party in "Recommendations for measurement standards in quantitative electrocardiography", European Heart Journal (1985), vol. 6, pages 815 to 825 and in "Common Standards for Quantitative Electrocardiography: Goals and Main Results" by J. L. Willems et al. for the CSE Working Party in Methods of Information in Medicine (1990) vol. 29, No. 4, pages 263 to 271, the entire contents of each of which are hereby incorporated herein by reference.

The heartbeat data HBTB acquired in this way makes it possible to convert the blood flow signal 35 (BCS) and the injection protocol 47 ($IF_{TB}(t)$) into the heartbeat domain, as shown above by reference to FIGS. 5 and 6. To this end, the blood flow signal 35 (BCS) and the injection protocol 47 ($IF_{TB}(t)$) are fed into an AIR algorithm 42 which firstly carries out these conversions, taking account of the heartbeat data 41 ($HB_{TB}$) which have also been fed in, and then calculates the individual patient function 43 ($AIR_{TB}(HB)$) in the heartbeat domain from these values using equation [2], depending on the heartbeat (wherein the function C(HB) is given by the blood flow behavior data BCS, converted into the heartbeat domain).

Subsequently, using the heartbeat-related individual patient function 43 ($AIR_{TB}(HB)$), a prediction can be made based on a mean CTA heart rate 44 ($HR_{CTA}(t)$) (in bpm) obtained shortly before the actual examination.

To this end, in the example embodiment according to FIG. 7, a corrected patient function 45 ($AIR_{CORR}(HB)$) is firstly calculated as follows:

$$AIR_{CORR}(t) = (HR_{CTA}/60) \cdot AIR_{TB}(HB/HR_{CTA} \cdot 60) \quad [11]$$

This equation applies, due to the conversion factor 60 when the time is measured, as usual, in seconds, and the heart rate is measured in bpm. Since the blood circulation of the patient is a closed system, when adapting the AIR curve over the width, the amplitude of the patient function should change reciprocally so that the area under the AIR curve remains constant. This is provided for in equation [11] by the prefactor ($HR_{CTA}/60$). Equation [11] is essentially a special case of equation [6'a].

Then, with the PRED algorithm 38, the prediction 39 ($C_{EP}(t)$) of the contrast medium behavior in the time domain is given by equation [5].

Figure 8:
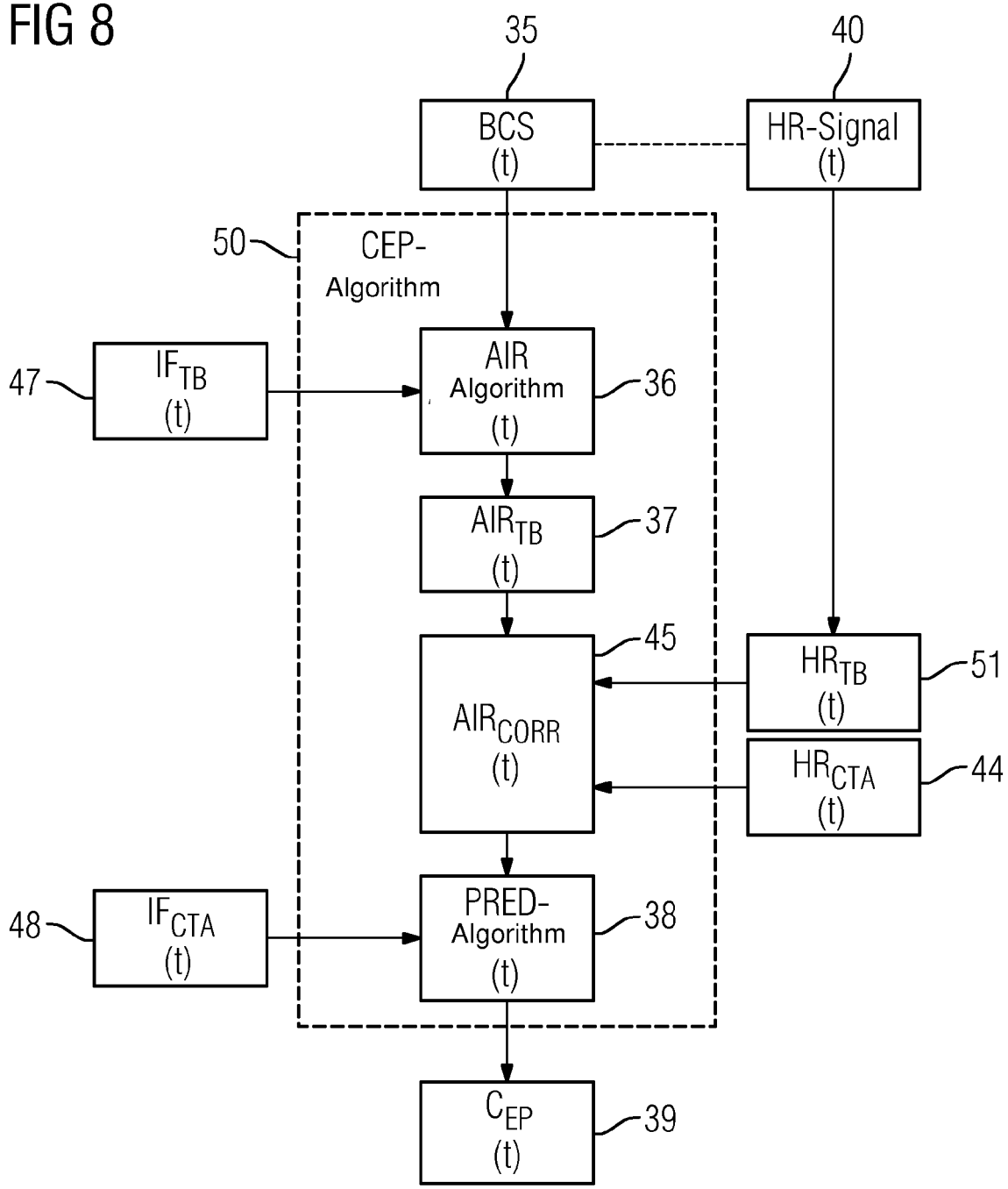
FIG. 8 is a representation of a second embodiment of a method according to the invention for predicting the contrast medium behavior.

FIG. 8 illustrates a second example of a method according to an embodiment of the invention wherein the implementation of the AIR algorithm does not enable the derivation of the individual impulse response function AIR to be calculated in the heartbeat domain, as was the case in FIG. 7, the HR signal is either an ECG signal from which the mean heart rate is calculated during the test bolus $HR_{TB}(t)$, or the mean heart rate $HR_{TB}(t)$ is used as given, for example, by a pulse meter, and the corrected prediction of the contrast medium behavior during the main scan is based on a mean heart rate ($HR_{CTA}(t)$) measured shortly before the main scan.

In this example, it is impossible, due to the implementation, to perform the calculation of the patient-specific impulse response function AIR in the HB domain because, for example, the AIR algorithm calculates in Fourier domain and, for this, homogeneous sampling of the signals may be required. Therefore, in this example, only the mean heart rate $HR_{TB}(t)$ during the test bolus can be inserted into the correction. For patients whose heart rate is regular but to whom medications which have lastingly reduced or increased the heart rate have been administered between the test bolus and the main scan, this example embodiment nevertheless leads to an improved prediction, even if not every heartbeat is taken into account.

According to an embodiment of the invention, in addition to the blood flow signal 35 (BCS(t)), a heart rate signal 40 is also determined, preferably simultaneously.

The individual patient function 37 ($AIR_{TB}(t)$) of a CEP algorithm 50 as a function of time is then calculated with the normal, unchanged, already existing AIR algorithm 36 and is subsequently simply transformed into a corrected patient function 45 ($AIR_{CORR}(t)$).

To this end, for example, an individual heartbeat-related patient function $AIR_{TB}(HB)$ could firstly be calculated in an intermediate step according to equations [3], [3'] or [3"]. This conversion of the derived patient function 37 $AIR_{TB}$, as a function of time, into a new patient function $AIR_{TB}(HB)$ as a function of the number of heartbeats, is shown graphically by FIG. 3. In this case, the curve shapes appear the same because the heart rate is assumed to be constant over time and is the mean heart rate. However, with a varying heart rate, and taking account of each individual heartbeat (FIG. 7), the curve shapes would have different forms. However, the function of the number of heartbeats $AIR_{TB}(HB)$ is independent of the heart rate.

This new (temporary) patient function $AIR_{TB}(HB)$ enables a change in the mean heart rate 44 ($HR_{CTA}(t)$) to be taken into account during the CTA scan. If it becomes apparent shortly before the CTA scan that the mean heart rate 44 ($HR_{CTA}(t)$) is significantly different from the mean heart rate 51 during the pre-measurement, then this conversion can take place, for example, according to equation [6], [6'], [6a] or [6'a], depending on which units are used for measuring and whether the corrected function should already contain the prefactor or whether the prefactor is later multiplied by the injection protocol in accordance with equation [9].

Particularly preferably, however, a time-related corrected patient function $AIR_{CORR}(t)$ can also be calculated without a prior conversion of the time-related patient function $AIR_{TB}(t)$ into a heartbeat-related patient function $AIR_{TB}(HB)$ according to equations [7] or [7a] directly from the time-related patient function $AIR_{TB}(t)$. As is evident, in this example embodiment, it is not necessary to make extensive changes to an existing CEP algorithm because the AIR algorithm 36 and the PRED algorithm 38 can remain unaltered and only in a new intermediate step must the individual impulse response function AIR be corrected. Calculation in the heartbeat domain is therefore not necessary in this example embodiment.

Figure 9:
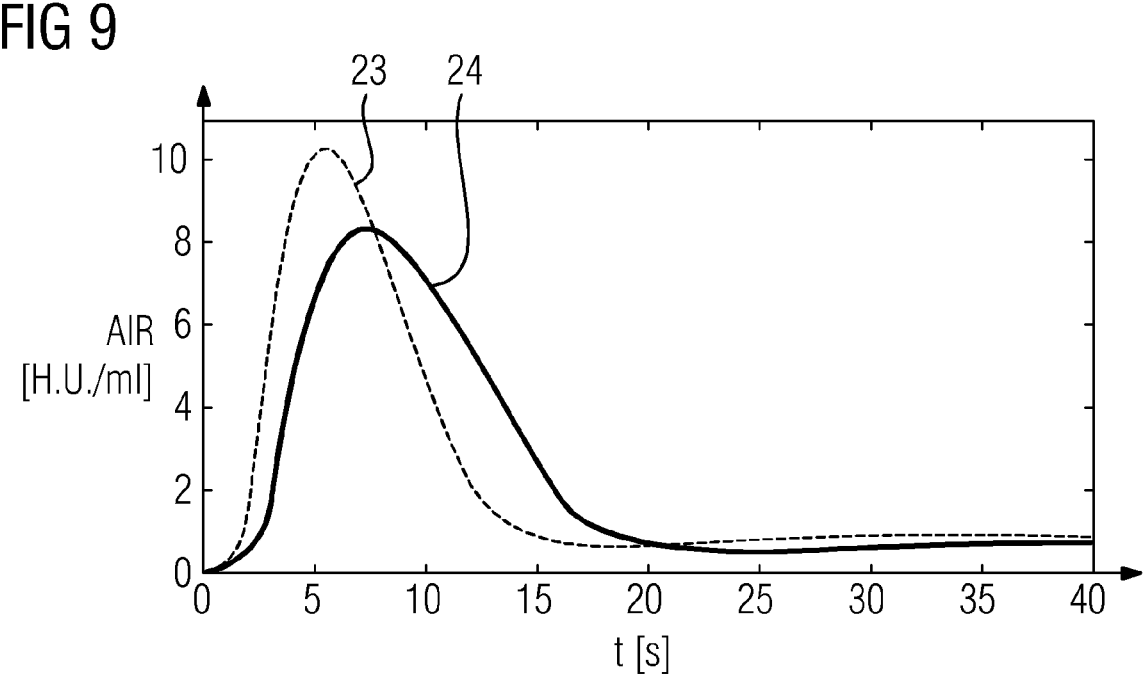
FIG. 9 is a graphical representation with an example of the second embodiment for adapting the derived patient function $AIR_{TB}(t)$ for changed heart rates.
Figure 10:
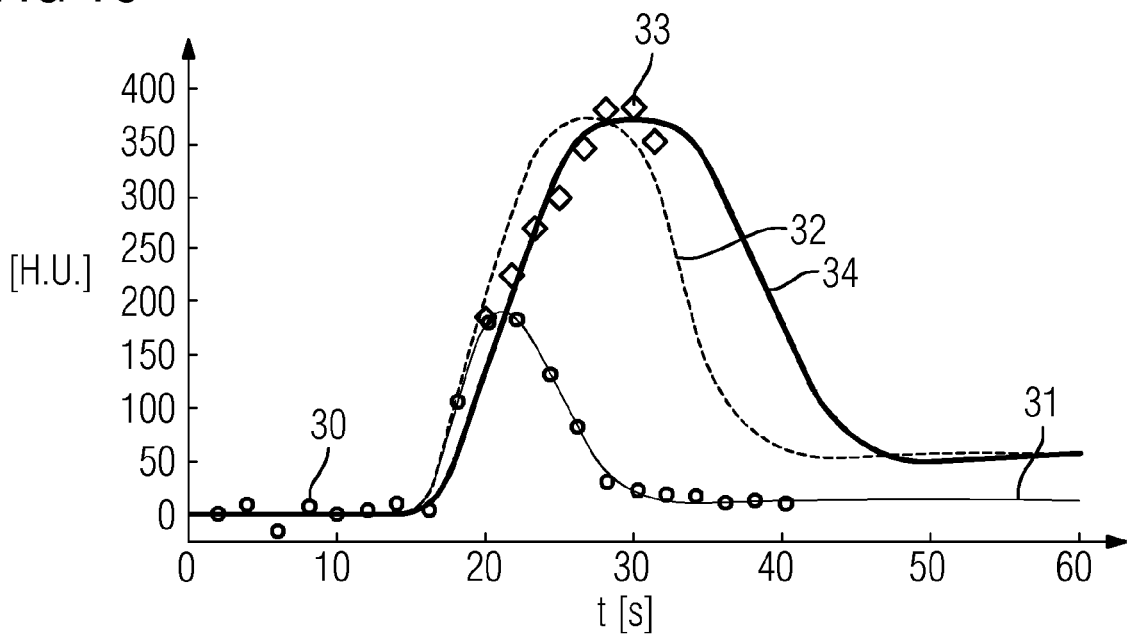
FIG. 10 is a graphical representation to describe the improvement in the prediction through the correction according to the second embodiment of the invention.

FIG. 9 shows, using the example of a 71-year old patient whose heart rate during the measurement of the test bolus 30 was 91 bpm and whose heart rate, after administration of a beta-blocker, had fallen to 74 bpm shortly before the CTA scan, the adaptation of the derived patient function $AIR_{TB}(t)$ 23 with a method according to FIG. 8, so that a corrected patient function 24 ($AIR_{CORR}(t)$) was obtained. This adapted patient function $AIR_{CORR}(t)$ led, in this patient, to a markedly improved prediction of the contrast medium behavior, as FIG. 10 shows.

This will now be described in greater detail making reference to FIG. 10. This example embodiment relates to the mean heart rate during the test bolus measurement and shortly before the CTA scan. The points (○ ○ ○) indicate the contrast medium accumulation 30 of the measured test bolus (TB). A curve fit 31 was determined with an AIR algorithm which represents the function $IF_{TB}(t) \otimes AIR_{TB}(t)$ from equation [1]. The dashed curve represents an uncorrected CTA prediction 32 derived therefrom. The points (◊ ◊ ◊) represent the measured CTA contrast medium accumulation 33. The continuous curve represents a corrected CTA prediction 34 derived from the function $AIR_{CORR}(t)$ 24.

If the two predictions, the uncorrected CTA prediction 32 and the corrected CTA prediction 34, are compared with the actually measured CTA contrast medium accumulation 33, it is immediately apparent that the corrected CTA prediction 34 of the measured CTA contrast medium accumulation 33 comes closer and is therefore better or more accurate.

Figure 11:
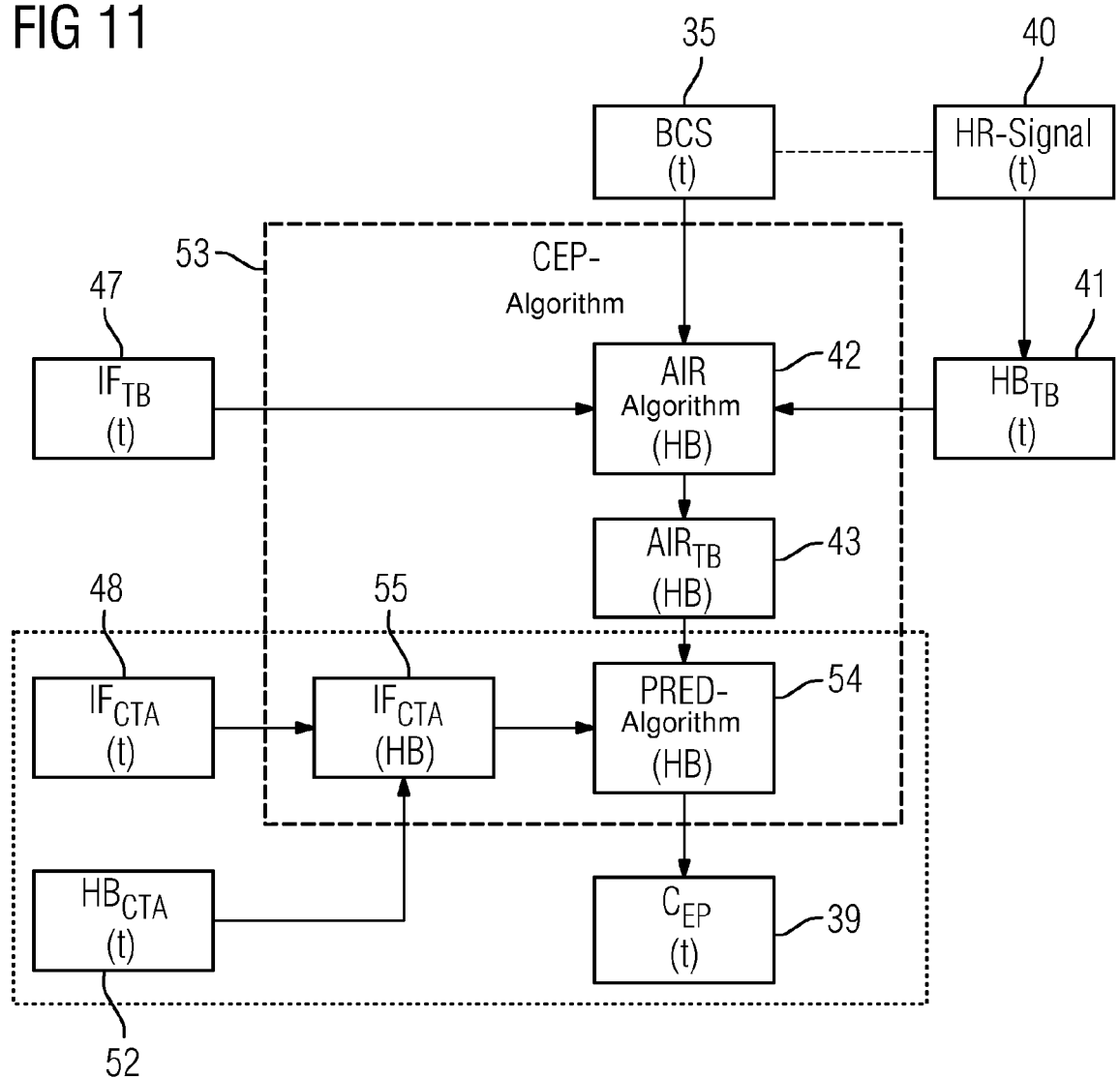
FIG. 11 is a representation of a third embodiment of a method according to the invention for predicting the contrast medium behavior in the heart rate domain.

Finally, FIG. 11 shows a third example of a method according to an embodiment of the invention, wherein
the implementation of the AIR algorithm permits derivation of the individual impulse response function AIR in the heartbeat domain (HB) rather than in the time domain (t),
the HR signal is an ECG signal wherein each individual heartbeat can be taken into account, and
the corrected prediction of the contrast medium behavior during the main scan is based on a heart rate signal ($HR_{CTA}(t)$) measured in the form of an ECG during the main scan.

For patients with a very irregular heart rate, this example embodiment is particularly advantageous since each individual heartbeat that has been measured during the test bolus measurement and during the later contrast medium-assisted measurement, is included in the calculation.

This example embodiment relates to an updating of the prediction after each individual heartbeat of the current ECG during the main examination. Herein, the derivation of the individual patient function $AIR_{TB}(HB)$ is carried out as in the example embodiment according to FIG. 7. Alternatively, both here and in the example embodiment according to FIG. 7, the blood flow signal BCS(HB) could also be recorded directly dependent on the heartbeat and the injection protocol $IF_{TB}$(HB) could be not time-controlled, but rather heartbeat-controlled. In this case, the AIR algorithm 42 receives all the information in the heartbeat domain.

As distinct from the example embodiment according to FIG. 7, the prediction of the contrast medium behavior is now carried out continuously updated based on the heart rate which is continuously measured during the contrast medium-assisted examination or on the current heartbeat 52 ($HB_{CTA}$(t)) of the patient, which is acquired using the ECG.

To this end, the current injection protocol $IF_{CTA}(t)$, where time-controlled, is converted to a heartbeat-related injection protocol 55 ($IF_{CTA}$(HB)). Furthermore, the CEP algorithm 53 and thus the PRED algorithm 54 must be able to calculate the prediction within the heartbeat domain and sufficient computer resources must be made available in order to be able to calculate the prediction in real time.

In further alternatives (not shown here) the procedure followed is in accordance with FIGS. 7 and 8, although the current heart rate is continuously updated during the contrast medium-assisted examination (for example, by calculation of a new mean value with each heartbeat) and the contrast medium behavior prediction is updated accordingly.

In order to carry out the various method variants, the device 60 for predicting a likely contrast medium behavior $C_{EP}$, as shown in FIG. 1 within the control device 12, comprises the following components:
an input interface 61, with which the patient-specific blood flow behavior data 35 are detected,
an impulse response function determining unit 62 which is configured to be able to determine an individual impulse response function 37, 43 from these blood flow behavior data 35,
an input interface 63 for detecting the heart rate signal 40, 44, 52,
a calculation unit 64 which is configured in order, for example, to predict the likely contrast medium behavior $C_{EP}$ according to one of the above method variants, and
an output interface 65 in order to transfer the likely contrast medium behavior $C_{EP}$ to other components.

If a heartbeat-related impulse response function AIR(HB) is to be stored or transferred for later use, this could also be carried out via the output interface 65 (which is configured in a suitable manner for this purpose) or via a separate output interface (not shown in FIG. 1).

A precondition for all these example embodiments is always the detection of a suitable heart rate signal (e.g. by way of an ECG) in conjunction with the pre-measurement and shortly before or during the main CT examination. This enables the prediction to be made independently of the heart rate that existed during the pre-measurement. Variations in the heart rate and a lasting increase or reduction in the heart rate will then no longer impair the prediction.

The following apply herein:
1. There is a plurality of possibilities for calculating the heart rate, for example with ECG, a pulse meter or a blood pressure measuring device.
2. There is a plurality of possibilities for carrying out the measurement for determining the individual impulse response function AIR, for example, with a test bolus, or optically.
3. In the case of a test bolus measurement, there is a plurality of known algorithms which can derive a patient-specific impulse response function from the test bolus, as disclosed, for example, in the older patent application DE 10 2012 209 410.5, or a deconvolution in the Fourier domain or an analysis with a pharmacokinetic model.
4. Depending on the CEP, AIR and/or PRED algorithm that is available and on the type of HR signal (complete ECG or only information on the mean heart rate during acquisition), there are as many example embodiments as desired for correcting the prediction for varying heart rates. The implementation of the heart rate correction should be matched to each individual case.

5. This angiographic examination method according to the invention is not restricted solely to computed tomography, but can potentially also be used for other imaging methods such as magnetic resonance tomography or ultrasonic tomography.

What is claimed is:

1. A method for prediction of a likely contrast medium behavior for a contrast medium-assisted examination of an object under investigation, comprising:
    detecting, by a processor, during a first time period associated with a pre-measurement based on a defined examination protocol, patient-specific blood flow behavior data;
    determining, by the processor, an individual impulse response function based on the blood flow behavior data associated with the pre-measurement;
    detecting, by the processor, during the first time period, a pre-measured heart rate signal associated with the pre-measurement;
    determining, by the processor, a heartbeat-related individual impulse response function based on the individual impulse response function and the pre-measured heart rate signal such that the heartbeat-related individual impulse response function represents the individual impulse response function depending on a heartbeat count;
    detecting, by the processor, during a second time period after the first time period, a currently detected heart rate signal associated with the contrast medium-assisted examination; and
    predicting, by the processor, the likely contrast medium behavior based on the heartbeat related individual impulse response function, a current examination protocol, and the currently detected heart rate signal.

2. The method of claim 1, wherein, firstly, a time-related individual impulse response function is determined and then, using the pre-measured heart rate signal, is converted into the heartbeat-related individual impulse response function.

3. The method of claim 2, wherein, based on the currently detected heart rate signal and the heartbeat-related individual impulse response function or the time-related individual impulse response function, a time-related corrected individual impulse response function is formed, and the prediction of the likely contrast medium behavior is carried out by combining the corrected impulse response function with the current examination protocol.

4. The method of claim 3, wherein, in order to form the corrected individual impulse response function, the heartbeat-related individual impulse response function is scaled with a time scaling factor which is given by an inverse value of a heart rate determined from the currently detected heart rate signal.

5. The method of claim 4, wherein, in order to form the corrected individual impulse response function, the scaled individual impulse response function is multiplied by the inverse value of the respective time scaling factor.

6. The method of claim 3, wherein, in order to form the corrected individual impulse response function, the time-related individual impulse response function is scaled with a time scaling factor which is given by a heart rate determined from the pre-measured heart rate signal in relation to a heart rate determined from the currently detected heart rate signal.

7. The method of claim 6, wherein, in order to form the corrected individual impulse response function, the scaled individual impulse response function is multiplied by an inverse value of the respective time scaling factor.

8. The method of claim 1, wherein the blood flow behavior data and the pre-measured heart rate signal are detected time-correlated.

9. The method of claim 1, wherein a recording of ECG data is made in order to detect the pre-measured heart rate signal.

10. The method of claim 9, wherein a mean heart rate existing during the pre-measurement is derived from the ECG data.

11. A method for activation of a medical imaging system, comprising:
    determining a reference time point for the imaging system, based on a start time point of a contrast medium administration and on a likely contrast medium behavior as predicted in claim 1.

12. A device configured to predict a likely contrast medium behavior for a contrast medium-assisted examination of an object under investigation, comprising:
    a processor configured to,
        detect, during a first time period associated with a pre-measurement based on a defined examination protocol, patient-specific blood flow behavior data,
        determine an individual impulse response function based on the blood flow behavior data associated with the pre-measurement,
        detect, during the first time period, a pre-measured heart rate signal associated with the pre-measurement,
        determine a heartbeat-related individual impulse response function based on the individual impulse response function and the pre-measured heart rate signal such that the heartbeat-related individual impulse response function represents the individual impulse response function depending on a heartbeat count,
        detect, during a second time period after the first time period, a currently detected heart rate signal associated with the contrast medium-assisted examination, and
        predict, the likely contrast medium behavior based on the heartbeat related individual impulse response function, a current examination protocol, and the currently detected heart rate signal.

13. A control device for an imaging system, comprising:
    a device having a processor configured to predict a likely contrast medium behavior by,
        detecting or outputting a contrast medium administration start time point,
        detecting, during a first time period associated with a pre-measurement based on a defined examination protocol, patient-specific blood flow behavior data,
        determining an individual impulse response function based on the blood flow behavior data associated with the pre-measurement,
        detecting, during the first time period, a pre-measured heart rate signal associated with the pre-measurement,
        determining a heartbeat-related individual impulse response function based on the individual impulse response function and the pre-measured heart rate signal such that the heartbeat-related individual impulse response function represents the individual impulse response function depending on a heartbeat count,
        detecting, during a second time period after the first time period, a currently detected heart rate signal associated with the contrast medium-assisted examination, predicting, the likely contrast medium behavior based on the heartbeat related individual impulse response function, a current examination protocol, and the currently detected heart rate signal, and determining a reference time point for the imaging system based on the likely contrast medium behavior.

14. An imaging system for creating image data sets from the interior of an object under investigation, comprising:

the control device of claim 13.

15. A non-transitory computer readable medium including a computer program product, directly loadable into a memory store of a control system of an imaging system, the computer program product including program code segments that when executed by a processor in the control system, configures the processor to, detect, during a first time period associated with a pre-measurement based on a defined examination protocol, patient-specific blood flow behavior data, determine an individual impulse response function based on the blood flow behavior data associated with the pre-measurement, detect, during the first time period, a pre-measured heart rate signal associated with the pre-measurement, determine a heartbeat-related individual impulse response function based on the individual impulse response function and the pre-measured heart rate signal such that the heartbeat-related individual impulse response function represents the individual impulse response function depending on a heartbeat count, detect, during a second time period after the first time period, a currently detected heart rate signal associated with a contrast medium-assisted examination, and predict, a likely contrast medium behavior based on the heartbeat related individual impulse response function, a current examination protocol, and the currently detected heart rate signal.

\* \* \* \* \*